(12) United States Patent
Cytron et al.

(10) Patent No.: US 7,479,139 B2
(45) Date of Patent: Jan. 20, 2009

(54) APPARATUS AND METHOD FOR PROTECTING TISSUES DURING CRYOABLATION

(75) Inventors: Samuel Cytron, Yavne (IL); Paul Sofer, Zofit (IL); Doris Schechter, Zikhron Yakov (IL); Uri Amir, Or Yehuda (IL); Roni Zvuloni, Haifa (IL)

(73) Assignee: Galil Medical Ltd., Yokneam (IL)

( * ) Notice: Subject to any disclaimer, the term of this patent is extended or adjusted under 35 U.S.C. 154(b) by 35 days.

(21) Appl. No.: 10/412,330

(22) Filed: Apr. 14, 2003

(65) Prior Publication Data

US 2004/0024391 A1 Feb. 5, 2004

Related U.S. Application Data

(63) Continuation-in-part of application No. PCT/IL02/01062, filed on Dec. 31, 2002.

(60) Provisional application No. 60/344,369, filed on Jan. 4, 2002.

(51) Int. Cl.
*A61B 18/02* (2006.01)

(52) U.S. Cl. .......................... 606/21; 606/20

(58) Field of Classification Search ............. 606/20–27, 606/41; 128/898
See application file for complete search history.

(56) References Cited

U.S. PATENT DOCUMENTS

| | | | |
|---|---|---|---|
| 3,298,371 A | | 1/1967 | Lee |
| 3,948,269 A | | 4/1976 | Zimmer |
| 4,519,389 A | * | 5/1985 | Gudkin et al. ............... 606/20 |
| 5,452,582 A | * | 9/1995 | Longsworth ................ 62/51.2 |
| 5,522,870 A | * | 6/1996 | Ben-Zion ..................... 607/104 |
| 5,800,487 A | * | 9/1998 | Mikus et al. ................ 607/105 |
| 5,800,488 A | * | 9/1998 | Crockett ..................... 607/105 |
| 5,860,970 A | | 1/1999 | Goddard et al. |
| 5,899,897 A | * | 5/1999 | Rabin et al. .................. 606/21 |
| 5,906,612 A | | 5/1999 | Chinn |
| 6,017,337 A | * | 1/2000 | Pira ............................ 606/20 |
| 6,017,361 A | | 1/2000 | Mikus et al. |
| 6,142,991 A | | 11/2000 | Schatzberger |

(Continued)

FOREIGN PATENT DOCUMENTS

WO WO 03/059247 7/2003

(Continued)

OTHER PUBLICATIONS

Gage et al. "Cryosurgery—A Review of Recent Advances and Current Issues", CryoLetters, 23: 69-78, 2002.

(Continued)

*Primary Examiner*—Henry M Johnson, III (57) ABSTRACT

An apparatus and method for protecting the neurovascular bundle during cryoablation of tissues of the prostate by heating the vicinity of the neurovascular bundle while cooling pathological tissues of a prostate to cryoablation temperatures, thereby cryoablating pathological tissues while protecting the neurovascular bundle from damage. A cryoprobe operable to cool a distal operating tip while heating a proximal shaft is presented.

9 Claims, 9 Drawing Sheets

U.S. PATENT DOCUMENTS

| | | | |
|---|---|---|---|
| 6,161,543 A * | 12/2000 | Cox et al. | 128/898 |
| 6,270,493 B1 | 8/2001 | Lalonde et al. | |
| 6,379,348 B1 * | 4/2002 | Onik | 606/21 |
| 6,419,690 B1 | 7/2002 | Mikus et al. | |
| 6,505,629 B1 * | 1/2003 | Mikus et al. | 128/898 |
| 2001/0021847 A1 * | 9/2001 | Abboud et al. | 606/21 |
| 2001/0037812 A1 | 11/2001 | Dobak, III et al. | |
| 2004/0024391 A1 | 2/2004 | Cytron et al. | |

FOREIGN PATENT DOCUMENTS

| | | |
|---|---|---|
| WO | WO 2004/089183 | 10/2004 |

OTHER PUBLICATIONS

Clarke et al. "Chemo-Cryo Combination Therapy: An Adjunctive Model for the Treatment of Prostate Cancer", Cryobiology, 42: 274-285, 2001.

Hollister et al. "Effects of Freezing on Cell Viability and Mechanisms of Cell Death in A Human Prostate Cancer Cell Line", Molecular Urology, 2(1): 13-18, 1998.

Chosy et al. "Monitoring Renal Cryosurgery: Predictors of Tissue Necrosis in Swine", The Journal of Urology, 159: 1370-1374, 1998.

* cited by examiner

APPARATUS AND METHOD FOR PROTECTING TISSUES DURING CRYOABLATION

This application is a Continuation-In-Part (CIP) of PCT Patent Application No. PCT/IL02/01062, filed on Dec. 31, 2002, which claims priority from U.S. Provisional Patent Application No. 60/344,369, filed on Jan. 4, 2002, the contents thereof are incorporated herein by reference.

FIELD AND BACKGROUND OF THE INVENTION

The present invention relates to an apparatus and method for protecting the neurovascular bundle during cryoablation of tissues of the prostate. More particularly, the present invention relates to heating the vicinity of the neurovascular bundle while cooling pathological tissues in or near the prostate to cryoablation temperatures, thereby cryoablating pathological tissues while protecting the neurovascular bundle from damage. Additionally, the present application relates to a cryoprobe having a distal treatment head and a proximal shaft, which shaft is designed and constructed to protect tissues adjacent to the shaft from damage by cooling induced by cold gases exhausting from the distal treatement head.

In recent years, cryoablation of pathological tissues has become an increasingly popular method of treatment of prostate cancer and of benign prostate hyperplasia ("BPH"). Cryoablation of pathological tissues is typically accomplished by utilizing imaging modalities such as x-ray, ultrasound, CT, and MRI to identify a locus for ablative treatment, then inserting one or more cryoprobes into that selected treatment locus, and cooling the treatment heads of those cryoprobes sufficiently to cause the tissues surrounding the treatment heads to reach cryoablation temperatures, typically below about −40° C. The tissues thus cooled are thereby caused to loose their functional and structural integrity. Cancerous cells cease growing and multiplying, and cryoablated tumor tissue material, whether from malignant tumors or from benign growths, is subsequently absorbed by the body. Cryoablation may thus be used to treat malignant tumors of the prostate, and to reduce prostate volume in cases of BPH.

The principle danger and disadvantage of cryosurgical ablative treatment of the prostate, however, is the danger of partially or completely destroying the functional and structural integrity of non-pathological tissues proximate to the treatment locus, thereby having a deleterious effect on the health and quality of life of the treated patient.

Various devices and methods have been proposed to enable cryoablation of pathological prostate tissue while limiting damage to non-pathological tissue. These fall roughly into two categories: devices and methods which protect tissues by preventing excessive cooling of those tissues during a cryoablation procedure in their vicinity, and methods devices and methods which enable accurate placement of cryoprobes used in cryoablation, so as to successfully concentrate the cooling effect of such cryoprobes at or near pathological tissue, thereby minimizing unwanted cooling of non-pathological tissue.

An example of the former category is the well-known technique of introducing a heating device or a heated fluid into the urethra of a patient, to heat the urethra and tissues adjacent to it during cryoablation of portions of the prostate, thereby helping to protect the urethra from damage while prostate tissues nearby are being cooled to cryoablation temperatures.

An example of the latter category is provided by U.S. Pat. No. 6,142,991 to Schatzberger. Schatzberger describes a high resolution cryosurgical method and device for treating a patient's prostate, including the steps of (a) introducing a plurality of cryosurgical probes to the prostate, the probes having a substantially small diameter, the probes being distributed across the prostate, so as to form an outer arrangement of probes adjacent the periphery of the prostate and an inner arrangement of probes adjacent the prostatic urethra; (b) producing an ice-ball at the end of each of said cryosurgical probes, so as to locally freeze a tissue segment of the prostate.

Schatzberger's apparatus includes (a) a plurality of cryosurgical probes of small diameter, the probes being for insertion into the patient's organ, the probes being for producing ice-balls for locally freezing selected portions of the organ; (b) a guiding element including a net of apertures for inserting the cryosurgical probes therethrough; and (c) an imaging device for providing a set of images, the images being for providing information on specific planes located at specific depths within the organ, each of said images including a net of marks being correlated to the net of apertures of the guiding element, wherein the marks represent the locations of ice-balls which may be formed by the cryosurgical probes when introduced through said apertures of the guiding element to said distinct depths within the organ.

Thus, Schatzberger's method and apparatus enable a surgeon to place a set of cryoablation probes within a prostate with relatively high accuracy, and to operate those probes to ablate selected tissues while avoiding, to a large extent, inadvertent and undesirable ablation of healthy tissues near the ablation site.

However, neither Schatzberger's technique nor any other known technique has proven sufficiently accurate to prevent damage to peripheral tissues in all cases. In particular, the neurovascular bundle, a prostatic area rich in blood vessels and in nerve tissues having cardinal importance in the process of erection of penis, is particularly vulnerable to damage by conventional prostatic cryoablation procedures. The neurovascular bundle lies dorsolateral to the prostate from the level of the seminal vesicles to the urethra, and is embedded in the lateral pelvic fascia along the pelvic side wall.

Damage to the neurovascular bundle may cause loss of sexual potency. Potent patients having an active sexual life are understandably reluctant to risk loss of potency as a result of cryosurgical treatment of the prostate, and such loss of potency unfortunately occurs in a non-negligible percentage of patients treated with conventional cryosurgery, as it does also in cases of treatment of prostate tumors by non-cryosurgical means.

Thus, there is a widely felt need for, and it would be highly advantageous to have, a therapeutic approach to malignant prostate tumors and to benign prostate hyperplasia, which approach enables cryoablation of prostate tissues while protecting the neurovascular bundle, thereby substantially reducing or eliminating the danger that cryosurgical treatment of the prostate will cause loss of erectile potency of the patient.

Similarly, there is a widely felt need for, and it would be highly advantageous to have, apparatus and method enabling selective protection of sensitive and functionally important healthy tissues in close proximity to pathological tissues whose cryoablation is desired, in numerous similar contexts.

Referring again to Schatzberger's technique, clinical practice has revealed an unanticipated limitation of that technique, with regard to implementation using a dense array of small diameter cryoprobes. As will be discussed in greater detail below, Schatzberger's technique provides for coordinated insertion of a multiplicity of parallel probes into an organ, and in particular provides for percutaneous insertion of multiple parallel cryoprobes, through the perineum of a patient, into a prostate. However, cold gases exhausting from treatment heads of cryoprobes cool the shafts of those cryoprobes. Body tissues lying alongside cryoprobe shafts, although distant from an intended cryoablation target, risk being damaged by cold induced by contact with, or proximity to, cryoprobe shafts cooled by gases exhausting from cryoprobe treatment heads, where those gases have been intensively cooled, typically either by evaporation or by expansion through a Joule-Thomson orifice.

Schatzberger's technique has proven an important contribution to cryoablation technology, in that it provides means for high-resolution cryoablation specifically adapted to the three-dimensional form of an intended ablation target. A Schatzberger template in current use today presents a 13 by 13 array of apertures for insertion of cryoprobes, the apertures being separated by 5 mm from each other, and each probe being of 1.5 mm in diameter. Yet, in practice, clinicians do not typically place cryoprobes in adjacent apertures when using Schatzberger's template, but rather typically leave one or even two vacant apertures between each aperture utilized to insert a cryoprobe.

Thus, in typical clinical practice today, Schatzberger's apparatus is utilized at a lower resolution than that of which the apparatus is mechanically capable. Aside from a natural desire on the part of the surgeon to minimize puncture trauma to the perineum, the practice of sparse, rather than dense, utilizing of Schatzberger's template has to do with undesired cooling induced in the shafts of the inserted cryoprobes during ablation of the intended target. When multiple parallel shafts of cryoprobes are densely introduced into a perineum or other area not intended for cryoablation, and each shaft is cooled by cold exhaust gases exhausting from a treatment head of a cryoprobe, the cumulative cooling effect of the dense array of shafts is to cool tissues proximate to the cryoprobe shafts to an extent which is damaging to those tissues. To avoid such damage using prior-art cryoprobes, clinicians are obliged to use Schatzberger's template at a lower resolution than would otherwise be possible.

There are, however, clinical indications that dense rather than sparse use of Shatzberger's template would be desirable. There is, first of all, the generally recognized purpose of that template as it was described by Schatzberger, namely using a dense array of probes to provide small iceballs from each probe, thus enhancing accuracy of the ablation and limiting ablation to the intended target. Clearly, the more densely packed the array, the smaller the iceball needing to be induced by each probe, and consequently the more accurate the match between the zone of induced ablation and the desired cryoablation target.

In addition, however, there are now clinical indications that effective cryoablation of cancer may require more intense cooling than that provided by standard cryoablation procedures in common practice today. Andrew A. Gage and John G. Baust, in an article entitled "Cryosurgery—A Review of Recent Advances and Current Issues" appearing in *CryoLetters* 23, 69-78 (2002) published by the Royal Veterinary College of London, reports experimental results obtained by Clarke and associates and reported in *Cryobiology* 42, 274-285, wherein surviving cancer cells were cultured from tissues subsequent to cryoablation at temperatures below $-50°$ C., despite the fact that temperatures below $-50°$ C. are generally considered to be adequate for complete ablation of tissue. Gage summarizes an in vitro investigation of a human prostate cell (PC3) line as follows: "Cell survival was evaluated by culture . . . when cell cultures were exposed to freezing to temperatures of $-25°$ C. to $-80°$ C., 90-99% loss of viability was produced, but some cells repopulated twelve days post-thaw. A temperature of $-100°$ C. was required to achieve total destruction." According to Gage, similar results are reported by Clarke et al. in *Mol Urol* 159, 1370-1374 and by Hollister et al. in *Mol Urol* 2, 13-18. Gage also cites seven studies substantiating his summary that "The incidence of persistent disease after cryotherapy vary with case selection and different physicians, but generally is about 10-30%, as manifested by prostate specific antigen (PSA) values and positive biopsies three to four years after treatment." These considerations, taken together, seem to indicate that improved cryoablation techniques are to be sought, both in ablation of prostate cancer and in other contexts.

It is generally recognized in cryoablation research and practice that the more intense the cold, the more reliable the ablation. It is further generally recognized that rapid cooling is an important factor in provoking cell death, a popular hypothesis being that rapid cooling encourages growth of intra-cellular ice crystals, known to be a powerful destructive agent, whereas gradual cooling tends to create extra-cellular ice crystals, which have some destructive effect but which are known to be less effective in ablation than are intra-cellular ice crystals.

It is further well known that proximity to a cryoprobe is a factor determining speed of cooling. Tissues adjacent to a rapidly cooled cryoprobe are cooled rapidly, whereas tissues more distant from a rapidly cooled cryoprobe are cooled more slowly.

Collectively, the above-mentioned clinical considerations give support for a hypothesis that massive rapid cooling by a dense array of small cryoprobes will provide improved survivability in cryoablation of prostate cancer and of cancers of other organs.

Yet, use of such a dense cooling array of cryoprobes cannot be undertaken with impunity under prior art methods and techniques such as those described by Schatzberger, because of the damage to tissues external to the intended cryoablation target, particularly damage to tissues cooled by proximity to a dense array of cryoprobe shafts transporting exhausting expanded cooling gases away from a dense array of cryoprobe treatment heads.

Thus there is a widely recognized need for, and it would be highly desirable to have, apparatus and method enabling cooling of cryoprobe treatment heads while preventing cooling of tissues adjacent to cryoprobe shafts, particularly in applications utilizing a dense array of cryoprobes.

In this context it is noted that U.S. Pat. No. 5,800,487 to Mikus et al. and U.S. Pat. No. 5,800,488 to Crockett teach a cryoprobe having a coolable treatment head comprising a heatable region, yet the probes mentioned therein do not comprise a heatable shaft, nor do they address, nor provide a solution to, the clinical need defined hereinabove. Additional art of relevance include U.S. Pat. No. 6,505,629 to Mikus et al.

SUMMARY OF THE INVENTION

According to one aspect of the present invention there is provided a method for protecting at least a portion of a neurovascular bundle while cryoablating tissues of a prostate, comprising (a) positioning an operating tip of a cryoprobe in a vicinity of pathological tissue within a prostate; (b) positioning a heating probe in a vicinity of a neurovascular bundle; and (c) heating the heating probe while cooling the operating tip of the cryoprobe to cryoablation temperatures, thereby cryoablating pathological tissue near the operating tip while preventing freezing of tissue of the neurovascular bundle near the heating probe; thereby preventing damage to at least a portion of the neurovascular bundle.

According to further features in preferred embodiments of the invention described below, the method further comprises utilizing imaging modalities to map the prostatic region of a patient, to locate pathological tissue to be cryoablated, and to locate a neurovascular bundle to be protected from cryoablation and from damage by freezing. Preferably, a guiding element is used to guide placement of a cryoprobe in a vicinity of the located pathological tissue, and to guide placement of the heating probe in a vicinity of the located neurovascular bundle.

According to still further features in the described preferred embodiments, the imaging modalities are selected from a group consisting of CT imaging, x-ray imaging, and ultrasound imaging. According to a preferred embodiment, ultrasound imaging of the prostate is obtained by insertion of an ultrasound probe into the rectum of a patient.

According to another aspect of the present invention there is provided a cryoprobe having a shaft and a distal operating tip, the tip being operable to cool to cryoablation temperatures tissues surrounding the tip, thereby cryoablating the tissues, the shaft being designed and constructed to protect tissues adjacent to the shaft from cryoablation and from damage by freezing.

According to further features in preferred embodiments of the invention described below, the shaft comprises an insulating element serving to thermally isolate cold regions within the shaft from external portions of the shaft having direct contact with tissues adjacent to the shaft. The insulating element may be formed as an insulating sheath comprising at least a partial vacuum.

According to further features in preferred embodiments of the invention described below, the shaft comprises a heating element, which may be an electrical resistance heating element, a microwave heating element, a radio frequency heating element, or a fluid heating module.

According to further features in preferred embodiments of the invention described below, the fluid heating module comprises a first passage for delivery of a fluid to a volume within the shaft, and further comprises a second passage for exhausting the fluid from said volume of said shaft. The first passage may be operable to deliver a pre-heated fluid to a portion of said shaft, or to deliver a compressed heating gas to a first Joule-Thomson orifice.

According to further features in preferred embodiments of the invention described below, the shaft comprises a first Joule-Thomson orifice and the operating tip comprises a second Joule-Thomson orifice. The cryoprobe comprises a first gas input passage and a second gas input passage, the first gas input passage being operable to deliver compressed heating gas to the first Joule-Thomson orifice while the second gas input passage delivers compressed cooling gas to the second Joule-Thomson orifice.

According to still another aspect of the present invention there is provided a method for protecting tissues adjacent to a shaft of a cryoprobe while cryoablating tissues adjacent to an operating tip of said cryoprobe, comprising (a) cooling the operating tip of the cryoprobe to cryoablation temperatures, thereby cryoablating tissues adjacent to the operating tip; and (b) simultaneously heating a portion of the shaft, thereby preventing freezing of tissues adjacent to the shaft, thereby protecting tissues adjacent to the shaft while cryoablating tissues adjacent to the operating tip.

A portion of the shaft, preferably the external portion adjacent to the external wall of the shaft, may be heated by electrical resistance heating, by microwave heating, by radio frequency heating, by circulating therein a pre-heated fluid, and by Joule-Thomson heating.

The present invention successfully addresses the shortcomings of the presently known configurations by providing an apparatus and method for protecting healthy and functionally important tissue areas during cryoablation of pathological tissues in their vicinity.

The present invention further successfully addresses the shortcomings of the presently known configurations by providing an apparatus and method for protecting the neurovascular bundle during cryoablation of nearby prostate tissues, thereby substantially reducing or eliminating the probability that loss of erectile potency of the patient will result from cryoablative prostate treatment.

The present invention further successfully addresses the shortcomings of the presently known configurations by providing an apparatus and method enabling cooling of cryoprobe treatment heads while preventing cooling of tissues adjacent to cryoprobe shafts, particularly in applications utilizing a dense array of cryoprobes.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention is of apparatus and method for protecting healthy tissues from damage, while cryoablating pathological tissues nearby. More particularly, the present invention relates to heating a first selected tissue area in or near a prostate, such as the neurovascular bundle area, while cooling to cryoablation temperatures a second selected tissue area in or near a prostate, such as benign or malignant tumor tissue, thereby cryoablating selected pathological tissues while protecting the neurovascular bundle or other selected healthy tissues from damage. The invention can be used to protect the neurovascular bundle during cryosurgery of prostate tissues, thereby reducing the risk of adverse effects of prostate cryosurgery to penile erectile functioning of a patent so treated.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

To enhance clarity of the following descriptions, the following terms and phrases will first be defined:

The phrase "heat-exchanging configuration" is used herein to refer to component configurations traditionally known as "heat exchangers", namely configurations of components situated in such a manner as to facilitate the passage of heat from one component to another. Examples of "heat-exchanging configurations" of components include a porous matrix used to facilitate heat exchange between components, a structure integrating a tunnel within a porous matrix, a structure including a coiled conduit within a porous matrix, a structure including a first conduit coiled around a second conduit, a structure including one conduit within another conduit, or any similar structure.

The phrase "Joule-Thomson heat exchanger" as used herein refers, in general, to any device used for cryogenic cooling or for heating, in which a gas is passed from a first region of the device, wherein it is held under higher pressure, to a second region of the device, wherein it is enabled to expand to lower pressure. A Joule-Thomson heat exchanger may be a simple conduit, or it may include an orifice through which gas passes from the first, higher pressure, region of the device to the second, lower pressure, region of the device. A Joule-Thomson heat exchanger may further include a heat-exchanging configuration, for example a heat-exchanging configuration used to cool gasses within a first region of the device, prior to their expansion into a second region of the device.

The phrase "cooling gasses" is used herein to refer to gasses which have the property of becoming colder when passed through a Joule-Thomson heat exchanger. As is well known in the art, when gasses such as argon, nitrogen, air, krypton, $CO_2$, $CF_4$, xenon, and $N_2O$, and various other gasses pass from a region of higher pressure to a region of lower pressure in a Joule-Thomson heat exchanger, these gasses cool and may to some extent liquefy, creating a cryogenic pool of liquefied gas. This process cools the Joule-Thomson heat exchanger itself, and also cools any thermally conductive materials in contact therewith. A gas having the property of becoming colder when passing through a Joule-Thomson heat exchanger is referred to as a "cooling gas" in the following.

The phrase "heating gasses" is used herein to refer to gasses which have the property of becoming hotter when passed through a Joule-Thomson heat exchanger. Helium is an example of a gas having this property. When helium passes from a region of higher pressure to a region of lower pressure, it is heated as a result. Thus, passing helium through a Joule-Thomson heat exchanger has the effect of causing the helium to heat, thereby heating the Joule-Thomson heat exchanger itself and also heating any thermally conductive materials in contact therewith. Helium and other gasses having this property are referred to as "heating gasses" in the following.

As used herein, a "Joule Thomson cooler" is a Joule Thomson heat exchanger used for cooling. As used herein, a "Joule Thomson heater" is a Joule Thomson heat exchanger used for heating.

In discussion of the various figures described hereinbelow, like numbers refer to like parts.

For purposes of better understanding the present invention, as illustrated in FIGS. 6-13 of the drawings, reference is first made to the construction and operation of conventional (i.e., prior art) cryosurgery apparatus and treatment method as illustrated in FIGS. 1-6.

Figure 1:
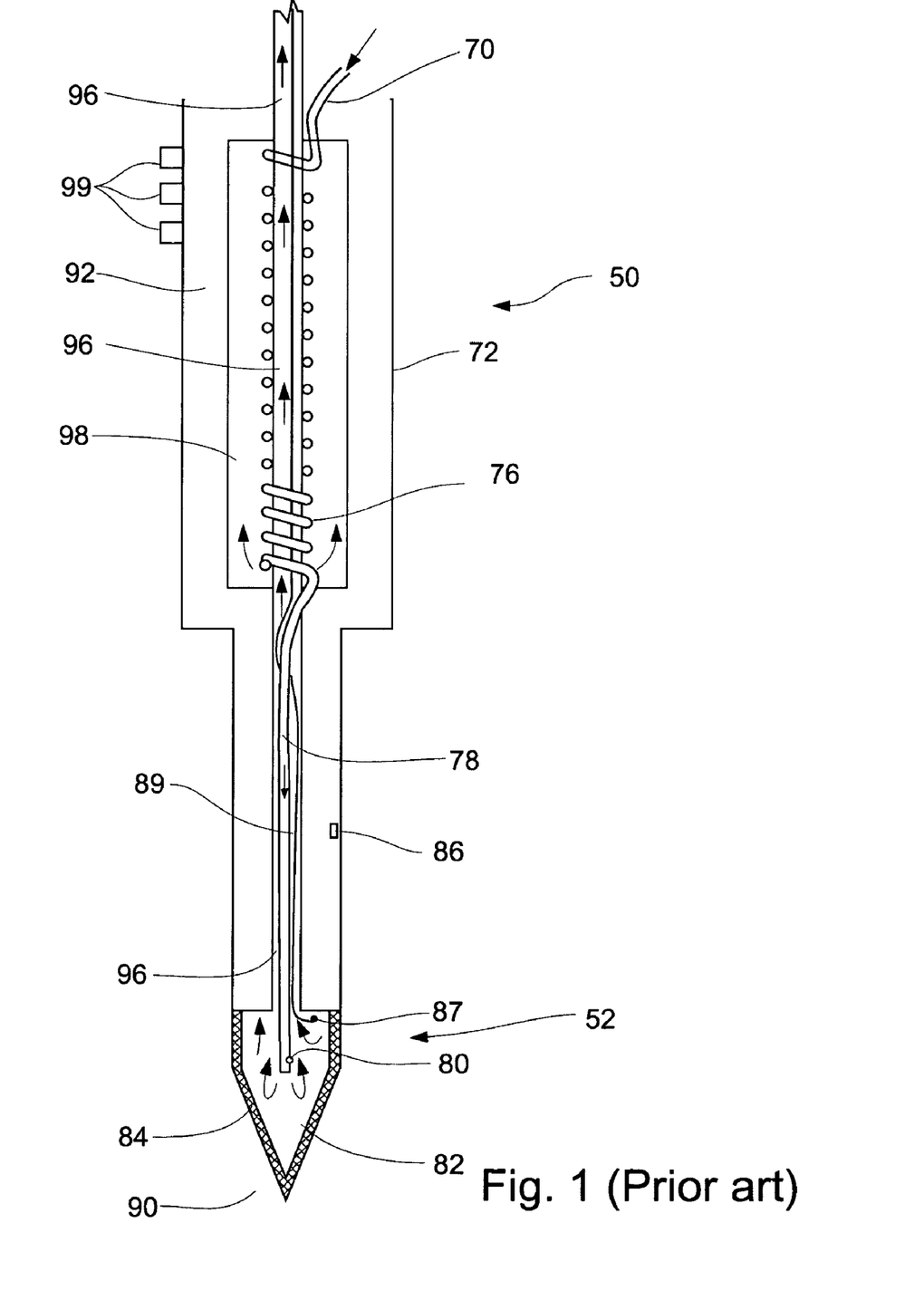
FIG. 1 is a simplified schematic of an exemplary cryoprobe, according to the methods of prior art.
Figure 2:
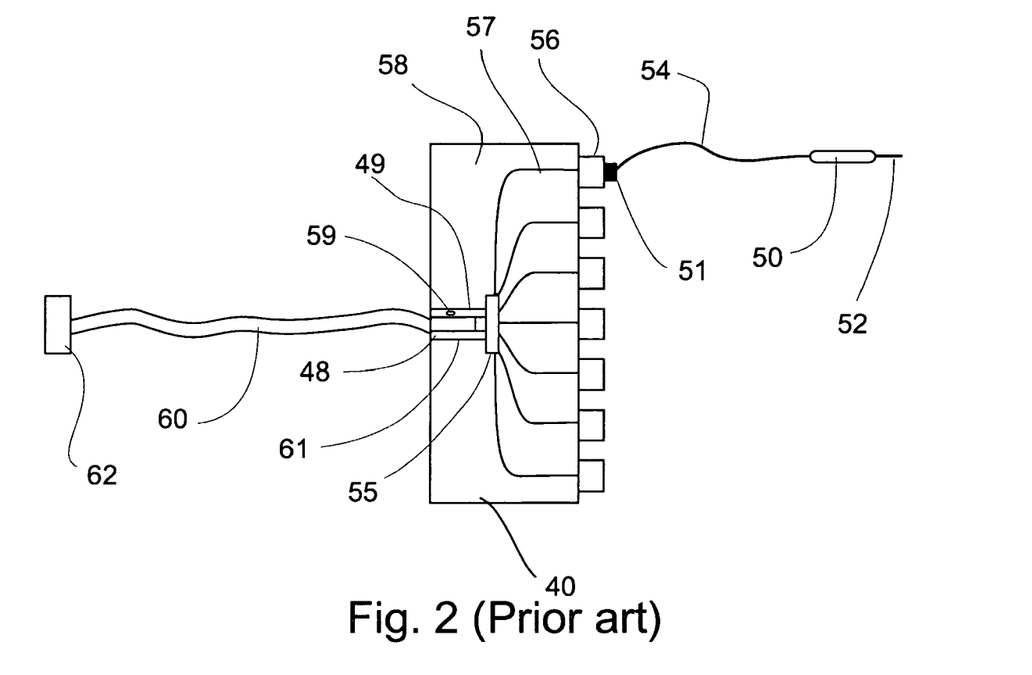
FIG. 2 is a simplified schematic of a manifold structure connecting a plurality of cryosurgical probes to a common gas source, according to the methods of prior art.
Figure 3:
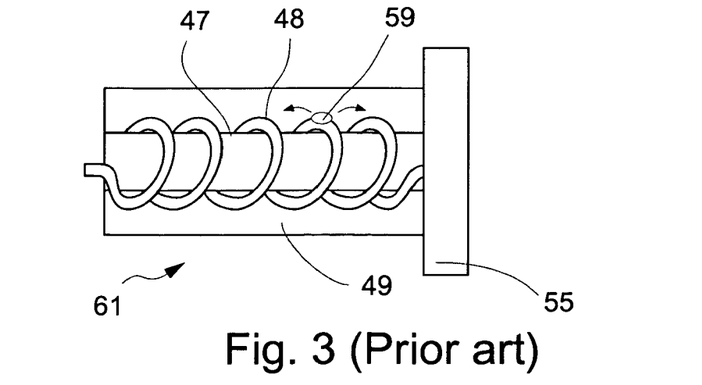
FIG. 3 is a simplified schematic of an alternative configuration of a pre-cooling element, according to the methods of prior art.

Referring to FIGS. 1-3, a cryosurgical apparatus according to methods of prior art includes a plurality of cryosurgical probes.

FIG. 1 presents a simplified schematic of an exemplary cryoprobe, according to the methods of prior art.

FIG. 1 presents a cryoprobe 50 having an operating tip 52 including a Joule-Thomson cooler for freezing a patient's tissue and a holding member 72 for holding by a surgeon. As shown in FIG. 1, operating tip 52 includes at least one passageway 78 extending therethrough for providing gas of high pressure to orifice 80 located at the end of operating tip 52, orifice 80 being for passage of high pressure cooling gas therethrough, so as to cool operating tip 52 and produce an ice-ball at its end 90.

When a high pressure cooling gas such as argon expands through orifice 80 it may liquefy, so as to form a cryogenic pool within chamber 82 of operating tip 52, which cryogenic pool effectively cools surface 84 of operating tip 52. Surface 84 of operating tip 52 is preferably made of a heat conducting material such as metal so as to enable the formation of an ice-ball at end 90 thereof.

Alternatively, a high pressure heating gas such as helium may be used for heating operating tip 52 via a reverse Joule-Thomson process, so as to enable treatment by cycles of cooling-heating, and further for preventing sticking of the probe to the tissue when extracted from the patient's body, and to enable fast extraction when so desired.

When a high pressure heating gas such as helium expands through orifice 80 it heats chamber 82, thereby heating surface 84 of operating tip 52.

Operating tip 52 includes at least one evacuating passageway 96 extending therethrough for evacuating gas from operating tip 52 to the atmosphere.

As shown in FIG. 1, holding member 72 may include a heat exchanger for pre-cooling the gas flowing through passageway 78. Specifically, the upper portion of passageway 78 may be in the form of a spiral tube 76 wrapped around evacuating passageway 96, the spiral tube being accommodated within a chamber 98. Thus, gas evacuated through passageway 96 may pre-cool the incoming gas flowing through spiral tube 76.

As further shown in FIG. 1, holding member 72 may include an insulating body 92 for thermally insulating the heat exchanger from the external environment.

Furthermore, operating tip 52 may include at least one thermal sensor 87 for sensing the temperature within chamber 82, the wire 89 of which extending through evacuating passageway 96 or a dedicated passageway (not shown). Probe 50 may further comprise one or more external thermal sensors 86, preferably placed at some distance from operating tip 52, operable to report on temperatures induced in surrounding tissues by cooling of operating tip 52.

In addition, holding member 72 may include a plurality of switches 99 for manually controlling the operation of probe 50 by a surgeon. Such switches may provide functions such as on/off, heating, cooling, and predetermined cycles of heating and cooling by selectively and controllably communicating incoming passageway 70 with an appropriate external gas container including a cooling or a heating gas.

Attention is now drawn to FIG. 2, which presents a simplified schematic of a gas distribution module connecting a plurality of cryosurgical probes 50 to a common gas source, according to the methods of prior art.

FIG. 2 presents a gas distribution module 40, wherein each of cryosurgical probes 50 is connected via a flexible connecting line 54 to a connecting site 56 on a housing element 58, preferably by means of a linking element 51. Cryosurgical probes 50 may be detachably connected to connecting sites 56.

Preferably, evacuating passageway 96 extends through connecting line 54, such that the outgoing gas is evacuated through an opening located at linking element 51 or at any other suitable location, e.g., manifold 55, see below. Preferably, line 54 further includes electrical wires for providing electrical signals to the thermal sensor and switches (not shown).

Each of cryosurgical probes 50 is in fluid communication with a manifold 55 received within a housing 58, manifold 55 being for distributing the incoming high pressure gas via lines 57 to cryosurgical probes 50.

As shown, housing 58 is connected to a connector 62 via a flexible cable 60 including a gas tube (not shown), connector 62 being for connecting the apparatus to a high pressure gas source and an electrical source.

The apparatus further includes electrical wires (not shown) extending through cable 60 and housing 58 for providing electrical communication between the electrical source and cryosurgical probes 50.

Preferably, housing 58 includes a pre-cooling element, generally designated as 61, for pre-cooing the high pressure gas flowing to cryosurgical probes 50. Preferably, pre-cooling element 61 is a Joule-Thomson cooler, including a tubular member 48 received within a chamber 49, tubular member 48 including an orifice 59 for passage of high pressure gas therethrough, so as to cool chamber 49, thereby cooling the gas flowing through tubular member 48 into manifold 55.

Attention is now drawn to FIG. 3, which presents an alternative configuration of a pre-cooling element 61 according to the methods of prior art, wherein tubular member 48 is in the form of a spiral tube wrapped around a cylindrical element 47, so as to increase the area of contact between tubular member 48 and the cooling gas in chamber 49.

According to yet another configuration (not shown), housing 58 includes a first tubular member for supplying a first high pressure gas to manifold 55, and a second tubular member for supplying a second high pressure gas to pre-cooling element 61. Any combination of gases may be used for cooling and/or heating the gases flowing through such tubular members.

Alternatively, a cryogenic fluid such as liquid nitrogen may be used for pre-cooling the gas flowing through housing 58. Alternatively, an electrical pre-cooling element may used for pre-cooling the gas.

Preferably, thermal sensors (not shown) may be located within cable 60 and manifold 55 for measuring the temperature of gas flowing therethrough.

Figure 4:
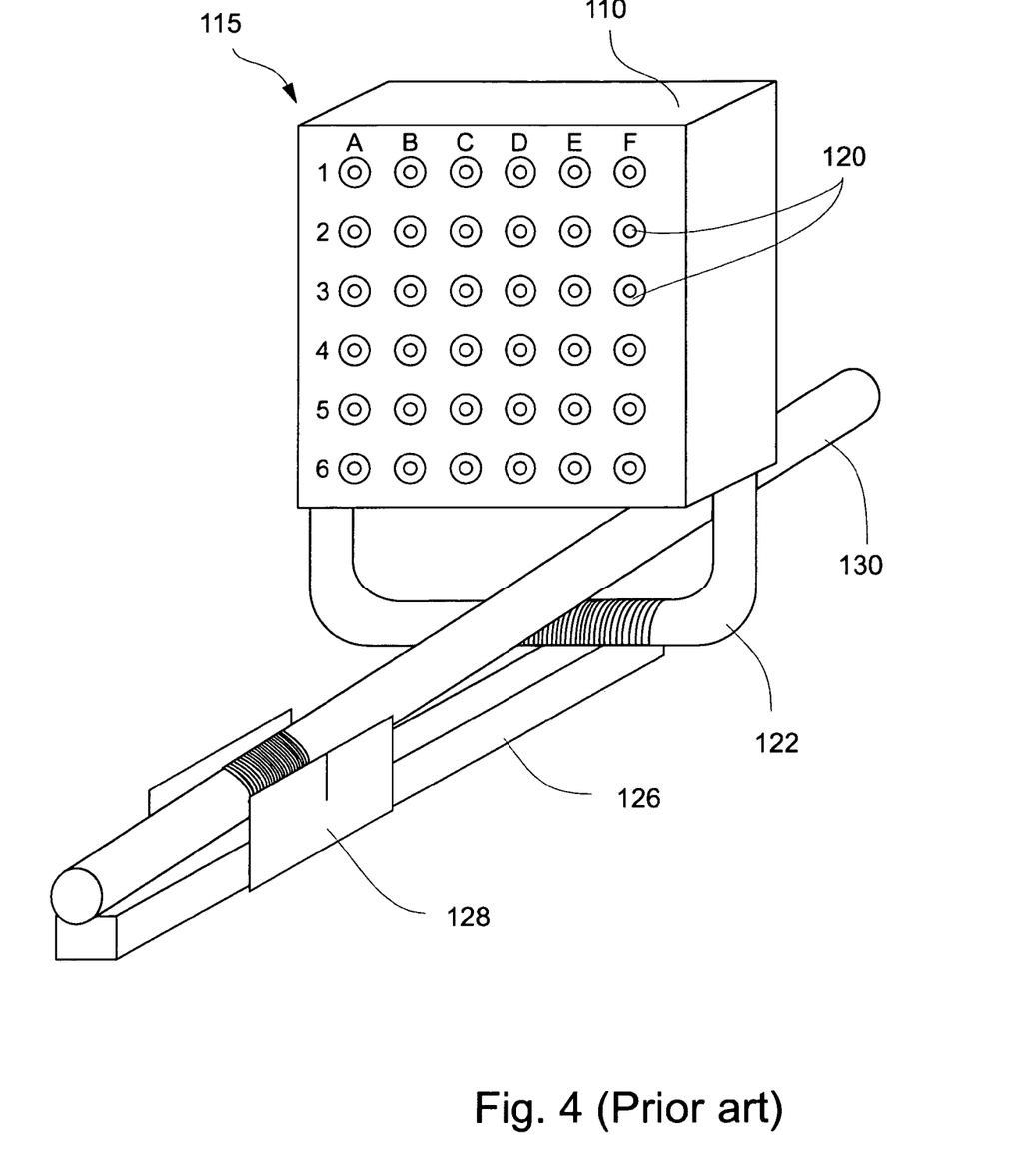
FIG. 4 is a simplified schematic of an apparatus comprising an ultrasound probe and a guiding element for guiding insertion of a plurality of cryoprobes into a patient's body, according to the methods of prior art.
Figure 5:
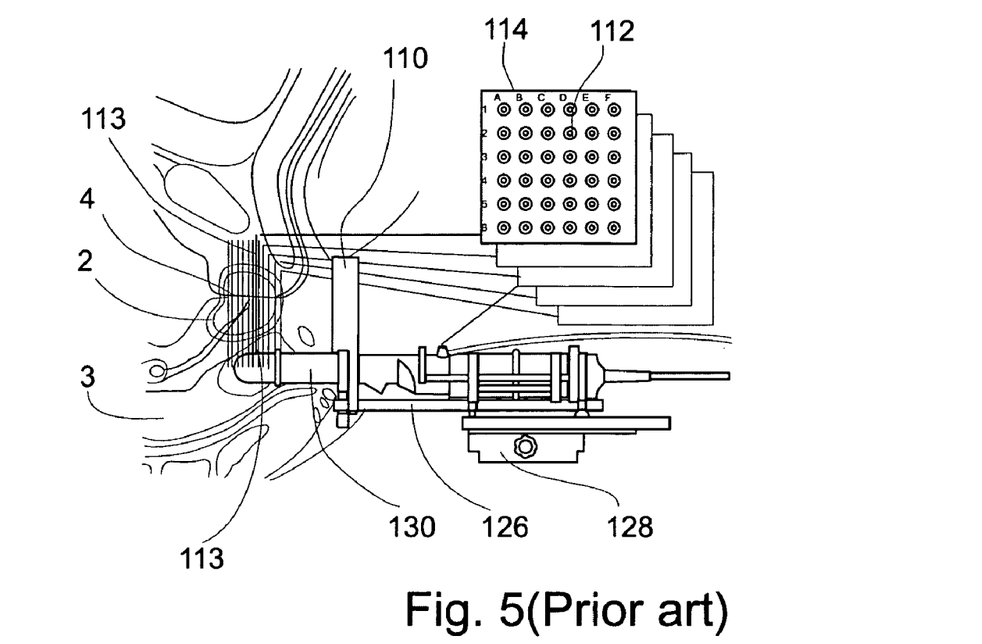
FIG. 5 is a simplified schematic showing a method of use of the apparatus presented in FIG. 4, according to the methods of prior art.
Figure 6:
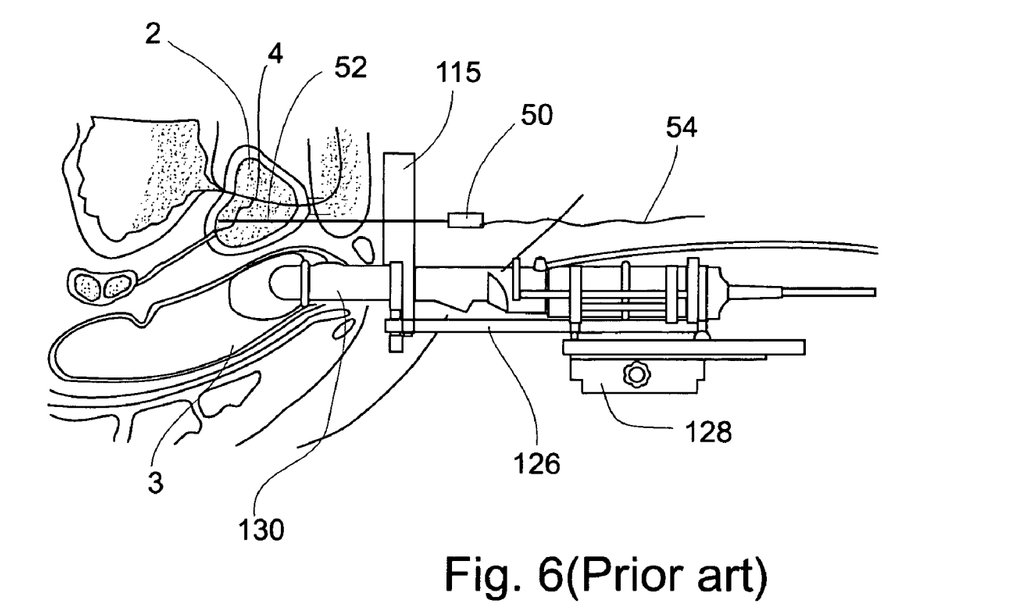
FIG. 6 is a simplified schematic showing a further step in the use of the apparatus presented in FIG. 4, according to the methods of prior art.

Attention is now drawn to FIGS. 4-6, which present a prior art method and apparatus utilizing an imaging device to form a three-dimensional grid of the patient's treated organ, e.g., prostate, the three dimensional grid serves for providing information on the three dimensional shape of the organ. Each of a set of cryosurgical probes is then inserted to a specific depth within the organ according to the information provided by the grid.

FIG. 4 is a simplified schematic of an apparatus comprising an ultrasound probe and a guiding element for guiding insertion of a plurality of cryoprobes into a patient's body, according to the methods of prior art.

As shown in FIG. 4, an ultrasound probe 130 is provided for insertion into the patient's rectum, ultrasound probe 130 being received within a housing element 128. A guiding element 115 is connected to housing element 128 by means of a connecting arm 126. As shown, guiding element 115 is in the form of a plate 110 having a net of apertures 120, each aperture serves for insertion of a cryosurgical probe therethrough. Preferably, the distance between each pair of adjacent apertures 120 is between about 2 millimeters and about 5 millimeters.

Attention is now drawn to FIG. 5, which is a simplified schematic showing a method of use of the apparatus presented in FIG. 4.

As shown in FIG. 5, ultrasound probe 130 is introduced to a specific depth 113 within the patient's rectum 3. A net of marks 112 is provided on the obtained ultrasound image 114, the net of marks 112 on image 114 being accurately correlated to the net of apertures 120 on guiding element 115.

Thus, marks 112 on image 114 sign the exact locations of the centers of ice-balls which may be formed at the end of the cryosurgical probes inserted through apertures 120 to the patient's prostate 2, wherein image 114 relates to a specific depth of penetration 113 of the cryosurgical probes into the prostate 2.

As shown in FIG. 5, ultrasound probe 130 is gradually introduced to various depths 113 of rectum 3, thereby producing a set of images 114, wherein each image relates to a respective depth of penetration into the prostate 2. Thus, each of images 114 relates to a specific plane perpendicular to the axis of penetration of the cryosurgical probes.

The set of images 114 provides a three dimensional grid of the prostate. Such three-dimensional grid is then used for planning the cryosurgical procedure.

For example, the introduction of a cryosurgical probe along a given axis of penetration to a first depth may effectively destroy a prostatic tissue segment, while introduction of the probe to a second depth may severely damage the prostatic urethra.

Since the ice-ball is locally formed at the end of the cryosurgical probe, each probe may be introduced to a specific depth so as to locally provide an effective treatment to a limited portion of the prostate while avoiding the damaging of non-prostatic or prostatic tissues located at other depths of penetration.

Attention is now drawn to FIG. 6, which is a simplified schematic presenting a further step in the use of the apparatus presented in FIG. 4, according to the methods of prior art.

FIG. 6 shows the insertion of an operating tip 52 of a cryosurgical probe 50 through an aperture of guiding element 115 into the prostate 2 of a patient.

Preferably, a plurality of cryosurgical probes are sequentially inserted through apertures 120 of guiding element 115 into the patient's prostate, wherein each probe is introduced to a specific depth, thereby providing substantially local effective treatment to distinct segments of the prostatic tissue while avoiding the damaging of other prostatic or non-prostatic tissue segments.

Preferably, each of the cryosurgical probes includes a scale for indicating the depth of penetration into the prostate.

Thus, it may be seen that the prior art apparatus and methods presented by FIGS. 1-6 enable diagnostic mapping of areas to be treated within a prostate, and further enable guiding a plurality of cryogenic probes into a prostate in such a manner that the cryogenic probes are placed according to the planned treatment areas so mapped.

Preferred embodiments of the present invention may now be described, utilizing the exemplary context of the prior art apparatus and methods described hereinabove and presented in FIGS. 1-6. It is noted, however, that the aforementioned prior art context is here described for exemplary purposes only. The invention disclosed herein is not limited to the exemplary context. In particular, alternative methods of diagnostic mapping may be utilized, such as x-ray mapping, CT mapping with or without use of a contrast medium, MRI mapping, ultrasound mapping not utilizing the anal probe described above, and others. Cryoprobes dissimilar to cryoprobe 50 presented in FIG. 1 may be utilized in embodiments of the present invention, on condition that they are capable of cooling tissues to cryoablation temperatures. Apparatus and methods other than those depicted in FIGS. 3-6 may be utilized to accurately deliver one or more cryoprobes to a selected locus for cryoablation of tissues thereat, and to accurately deliver one or more heating probes to selected locations for protecting healthy tissue from freezing, as will be explained hereinbelow.

Figure 7:
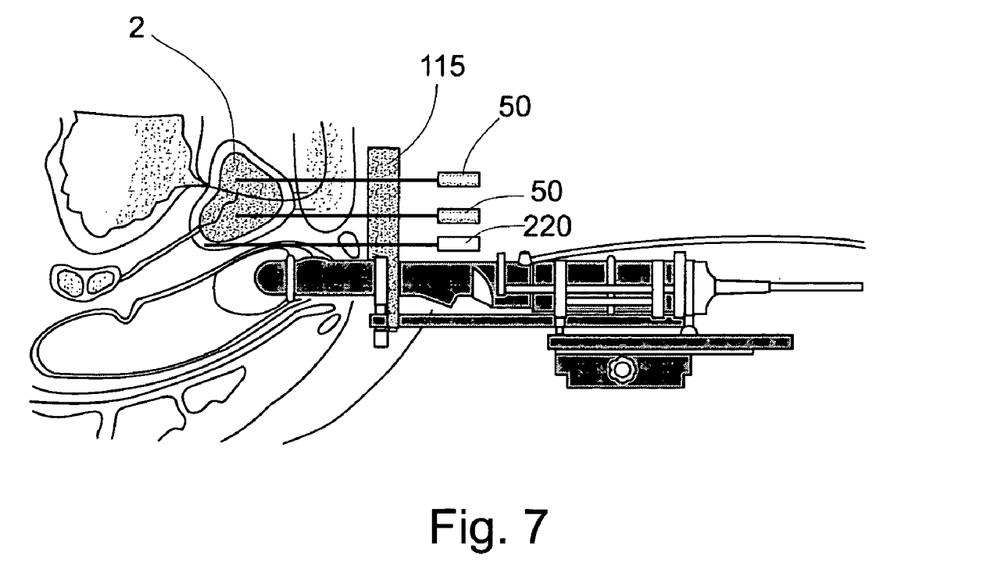
FIG. 7 is a simplified schematic representation of a prostrate treatment apparatus according to an embodiment of the present invention.

Attention is now drawn to FIG. 7, which is a schematic representation of a prostrate treatment apparatus according to a preferred embodiment of the present invention.

FIG. 7 is similar to FIG. 6 in all respects, which the exception of the presence of a heating probe 220 in addition to cooling probes 50. Heating probe 220 may be passed through guiding element 115 into a planned location in or near the prostate or other organ, where it may be used to heat tissues during cryoablation procedures. Thus, while cryoprobes 50 are cooled to cryoablated pathological tissues, heating probes 220 may be heated to protect nearby tissues from the destructive effects of cooling induced by cryoprobes 50.

Structurally, heating probes 220 may be similar or identical to cryoprobes 50 of FIG. 1 and to probes 50 of FIG. 2, and yet be differentiated by the fact that whereas cooling probes 50 are connected to a supply of cooling gas and use Joule-Thomson cooling to cool their operating heads to cryoablation temperatures, heating probes 220 are connected to a supply of heating gas and utilize Joule-Thomson heating to beat probes 220 during the surgical procedure, thereby protecting tissues in their vicinity from damage from cooling induced by cooling probes 50.

In alternate configurations, heating probes 220 may be heated by flow of pre-heated fluids, by electrical resistance heating, by microwave beating, by radio frequency heating, or by any other convenient form of heating. Yet, in a particularly preferred embodiment, identical probes connectable both to a cooling gas supply and to a heating gas supply may be utilized as cooling probes 50 in a first context, and as beating probes 220 in a second context. For example, a same probe may be utilized as cooling cryoprobes 50 at a first depth of penetration, and as heating probe 220 at a second depth of penetration.

Figure 8:
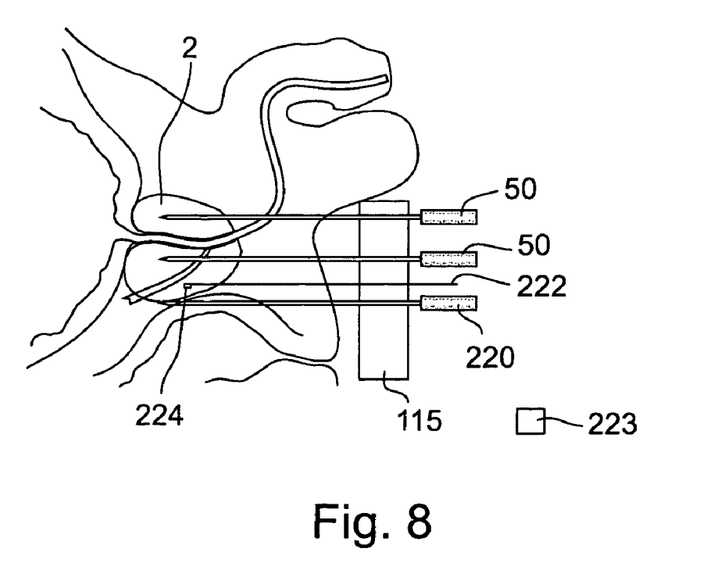
FIG. 8 is an additional view of the treatment apparatus of FIG. 7.

Attention is now drawn to FIG. 8, which is another simplified schematic representation of a prostrate treatment apparatus according to a preferred embodiment of the present invention. FIG. 8 is similar to FIG. 7, but additionally presents a thermal sensor unit 222, which may comprise a thermocouple 224. Thermal sensor unit 222 is shown having been placed between cryoprobes 50 and heating probes 220 in the prostate 2 of a patient, where it may be used to monitor temperature changes resulting from cooling of probes 50 and heating of probes 220. Data from thermal sensor unit 222, and from thermal sensors within probes 50 and 220, may be monitored by a control module 223, which may be operable to control heating of probes 220 and cooling of probes 50, based on data received from these thermal sensors, under algorithmic control.

Figure 9:
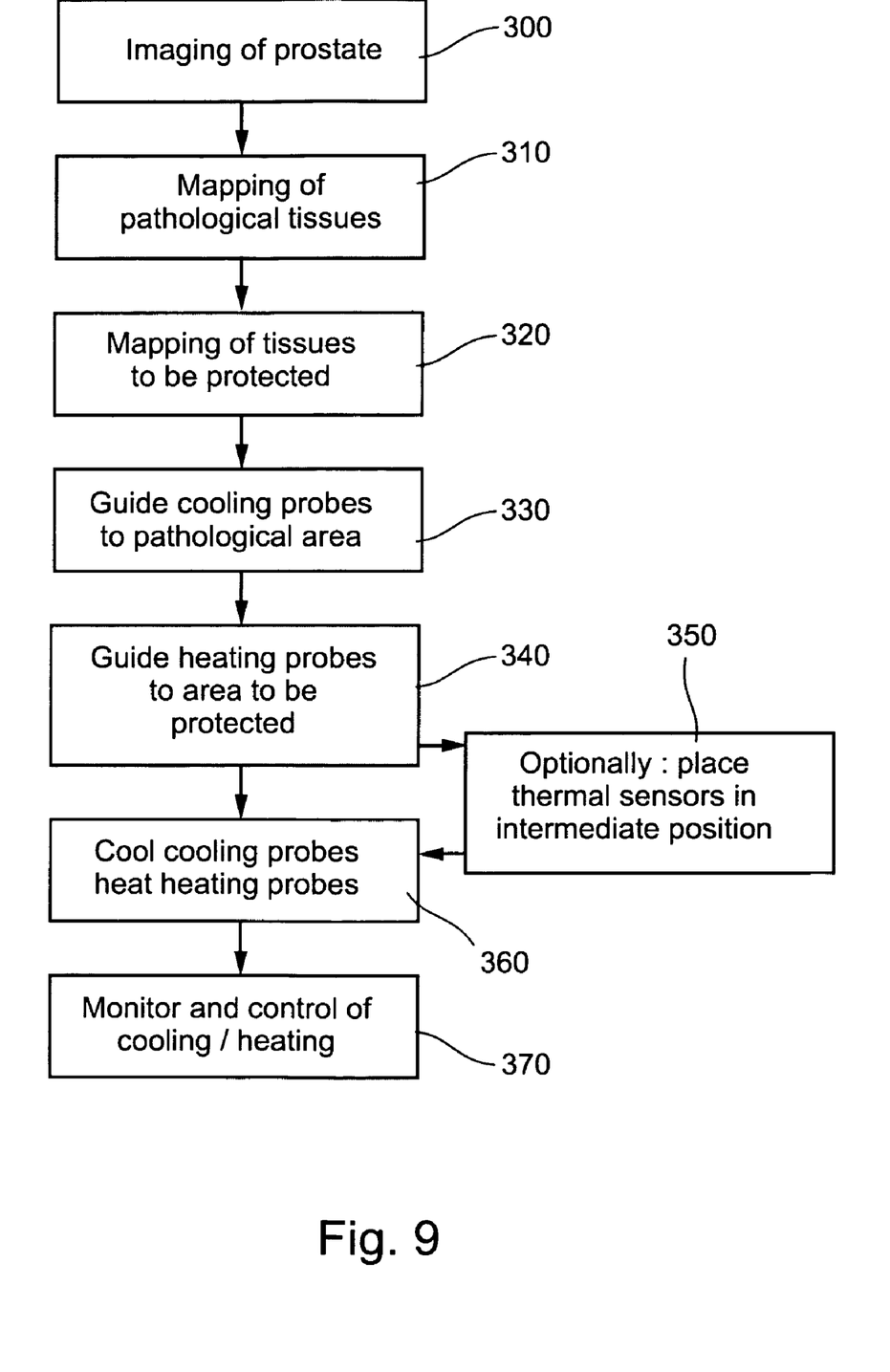
FIG. 9 is a simplified flow-chart of a recommended procedure for cryoablation of a portion of an organ, such as a tumor of a prostate, according to an embodiment of the present invention.

Attention is now drawn to FIG. 9, which is a simplified flow-chart of a recommended procedure for cryoablation of a portion of an organ, such as a tumor of a prostate. At step 300, an operator utilizes an imaging modality to image a prostate to be treated. Step 300 may be accomplished utilizing the anal ultrasound probe and methodology described by Schatzberger. Alternatively, other forms of ultrasound imaging, x-ray imaging, CT imaging (with or without use of contrast medium), MRI imaging, or yet other medical imaging modalities may be used to provide information concerning the prostate to be treated.

According to an embodiment of the present invention, utilization of the images gleaned from step 300 is twofold. At step 310, the images created at step 300 are inspected to determine the locus of the pathological tissues to be cryoablated is obtained, as described by Schatzberger. (Preferably, a three-dimensional mapping of the treatment locus is created.) At step 320, the images created at step 300 are further inspected and the position of the neurovascular bundles, or the position of other tissue which the surgeon desires to protect, is similarly determined and mapped.

At step 330, a guiding element such as guiding element 115 of FIG. 6 is used to guide cooling probes such as cooling probe 50 of FIG. 6 to the treatment locus found at step 310.

At step 340, a guiding element is similarly utilized to guide one or more heating probes 220 to the vicinity of the neurovascular bundles, or to the vicinity of other tissues which the surgeon desires to protect.

At optional step 350, a guiding element such as guiding element 115 may be used to place thermal sensor units 222 in intermediate positions between the desired locus of cryoablation and the position of the neurovascular bundle, or the position of other tissue which an operator desires to protect. Output from thermal sensors may then be monitored, at step 370 below.

At step 360, the surgeon operates cooling probes 50 to cool the pathological tissues to cryoablation temperatures, thereby cryoablating those pathological tissues, and also heats the heating probes placed in step 340, thereby protecting the neurovascular bundles or other selected tissues which the surgeon desires to protect.

At step 370, thermal sensors in cooling probes 50 and in heating probes 220 may be used to monitor the cooling of probes 50 and the heating of probes 220, which cooling and heating may be adjusted according to the data returned by these thermal sensors, thereby facilitating the adjustment of the cooling/heating process so as to optimize cryoablation while ensuring that the neurovascular bundle, or other protected tissues, are neither cooled to destructive temperatures, nor exposed to excessive heating. If external thermal sensors were placed in optional step 350, these too may be monitored to determine the temperature at a point or points between the cryoablation locus and the position of the protected tissue, and cooling of cooling probes 50 and heating of heating probe 220 may be adjusted accordingly, to optimize the desired effect.

Additionally, at step 370, imaging modalities such as ultrasound may be used to monitor the progression of freezing in the cryoablation process, and in particular to monitor the size and position of ice-balls formed around the operating heads of cooling probes 50, and in particular to monitor the effectiveness of the heating provided by heating probes 220 in limiting the progression of formation of ice balls (frozen tissue areas) in the vicinity of the neurovascular bundle or other protected areas.

Control of cooling of cooling probes 50 and heating of heating probes 220 may be managed manually by a surgeon based on monitoring images and data from thermal sensors in or near the probes. Alternatively, control of the heating and cooling of the probes may be managed by control unit 223, based on data received electronically from the thermal sensors, under algorithmic control.

Figure 10:
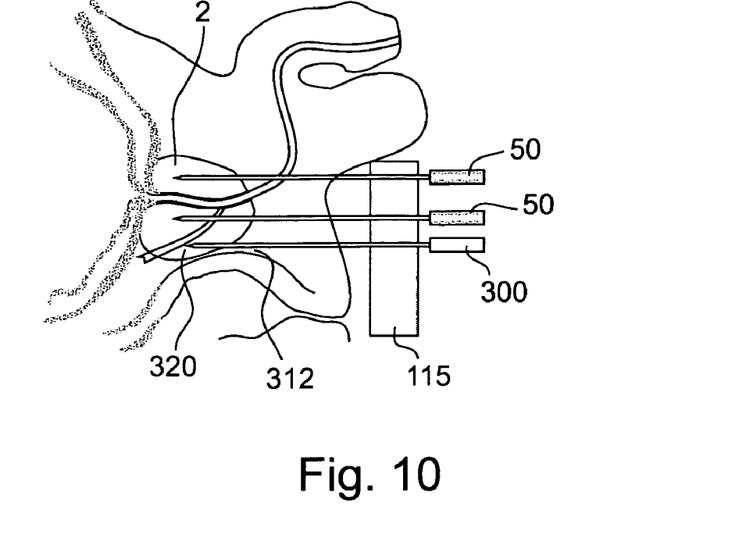
FIG. 10 is a simplified schematic representation of a prostrate treatment apparatus according to an additional preferred embodiment of the present invention.

Attention is now drawn to FIG. 10, which presents a simplified schematic representation of a prostrate treatment apparatus according to an additional preferred embodiment of the present invention.

Figure 11:
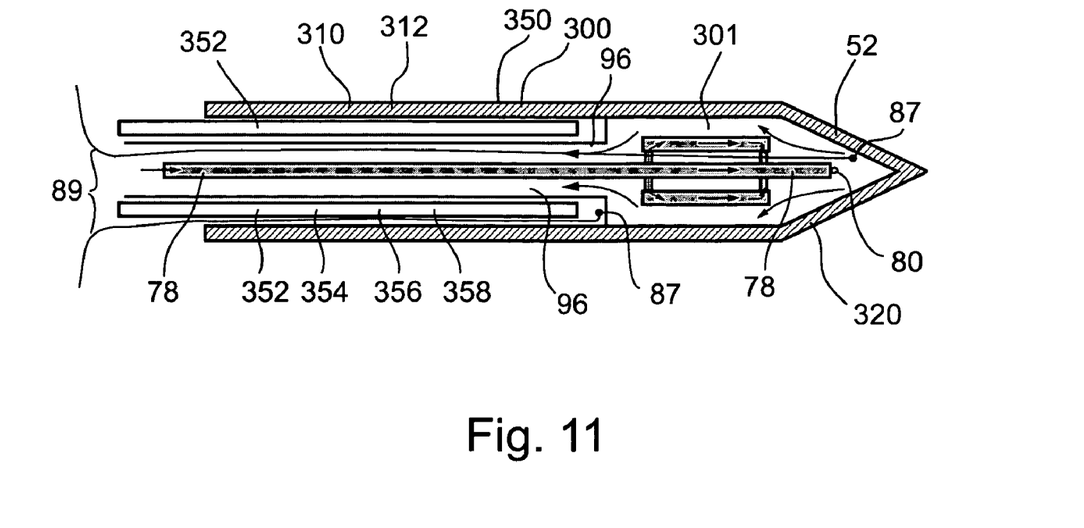
FIG. 11 is a simplified schematic of a cryoprobe comprising a cryogenic treatment head and a heatable shaft, according to an embodiment of the present invention.
Figure 12:
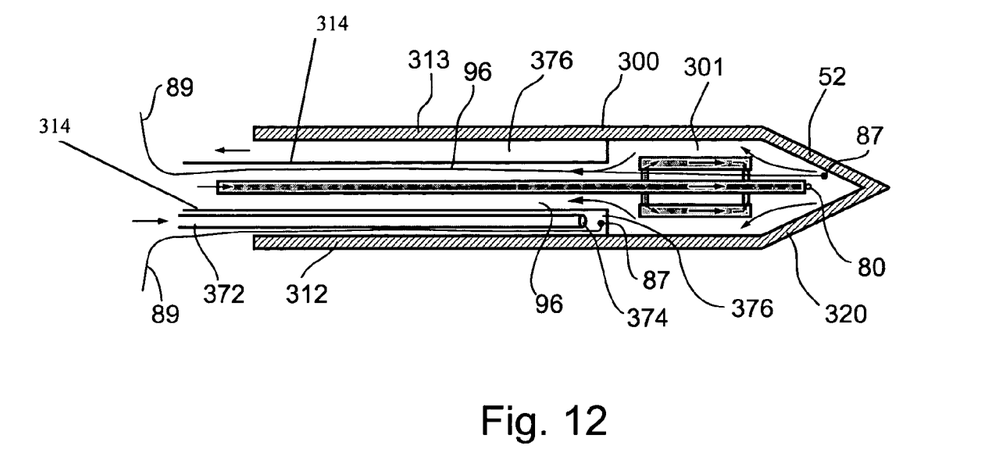
FIG. 12 is a simplified schematic of an alternative construction of a cryoprobe having a cryogenic treatment head and a heatable shaft, according to an embodiment of the present invention.
Figure 13:
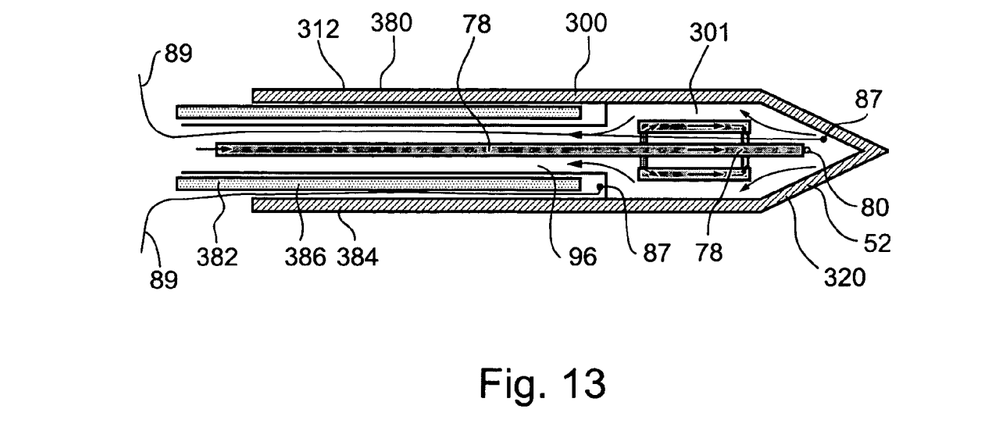
FIG. 13 is a simplified schematic of a cryoprobe having an insulated shaft, according to an embodiment of the present invention.

FIG. 10 presents a probe 300 whose position with respect to the patient's anatomy creates particular requirements, which probe 300 is designed to satisfy. It is to be noted that a distal portion 320 of probe 300 is placed within prostate 2, and may be thought of as being located in a region whose cryoablation is desired. Shaft portion 312 of probe 300, however, is adjacent to the patient's neurovascular bundle, which it is desired to be protected from freezing during cryoablation of the tissues surrounding distal portion 320. An optimal solution to the situation depicted in FIG. 10 requires that probe 300 be operable to cool distal portion 320, yet that tissues near shaft 312 be protected from freezing. FIGS. 11-13 present designs for a probe 300 that satisfies this requirement.

Attention is now drawn to FIG. 11, which is a simplified schematic of a cryoprobe having a cryogenic treatment head and a heatable shaft, according to an embodiment of the present invention.

FIG. 11 presents a cryoprobe 350 having a distal portion 320 implemented as a cryogenic operating tip 52, similar to that presented in FIG. 1 and discussed hereinabove. Probe 350 comprises a gas input passageway 78 operable to transport cooling gas, through a heat exchanging configuration 301, to a Joule-Thomson orifice 80 in operating tip 52, for cooling operating tip 52 as described with respect to FIG. 1. Expanded gas from operating tip 52 is exhausted through exhaust passageway 96. Probe 350 of FIG. 11 is distinguished from probe 50 of FIG. 1, however, by the presence of an electrical or electronic heating element 352 located in the proximal shaft portion 312 of probe 350. Heating element 352 may be implemented as an electrical heater resistance element 354, as a radio frequency heating element 356, as a microwave heating element 358, or as any other form of electrically powered heater. Probe 350 is thus operable to satisfy the requirements discussed above with respect to FIG. 10, in that operating tip 52 may be cooled to cryoablation temperatures, while shaft 312, corresponding to proximal portion 310 of probe 300 FIG. 10, is heated by heating element 352. Heating of element 352 protects tissues outside shaft 312 from being frozen by cold exhaust gasses in exhaust passageway 96. Heating element 352 also protects tissues outside shaft 312 from freezing when tissues surrounding operating tip 52 are cooled to cryoablation temperatures.

Attention is now drawn to FIG. 12, which is a simplified schematic of an alternative construction of cryoprobe 300, having a cryogenic treatment head and a heatable shaft, according to an embodiment of the present invention.

FIG. 12 presents a cryoprobe 370 having a distal portion 320 implemented as a cryogenic operating tip 52, similar to that presented in FIG. 1 and in FIG. 11, and discussed hereinabove. Probe 370 comprises a gas input passageway 78 operable to transport cooling gas, through a heat exchanging configuration 301, to a Joule-Thomson orifice 80 in operating tip 52, for cooling operating tip 52 as described with respect to FIG. 1. Expanded gas from operating tip 52 is exhausted through exhaust passageway 96. Probe 370 of FIG. 12 is distinguished from probe 350 of FIG. 11, however, in that shaft 312 of probe 370 is operable to be heated by a fluid heating process.

In one embodiment, pre-heated fluid may be supplied to probe 370 through input passageway 372, where it heats a portion of shaft 312 and is subsequently exhausted through exhaust passageway 376. Exhaust passageway 376 is preferably formed as a volume surrounding internal portions of shaft 312 that contain, in passageways 78 and 96, cold gasses transported to and from operating tip 52. Exhaust passageway 376 is also preferably formed so as to be contiguous to outer wall 313 of shaft 312. Preferably, a separator 314 which preferably comprises an insulating material (not shown) is interposed between exhaust passageway 376 and internal portions of shaft 312 such as cooling gas input passageway 78 and cooling gas evacuation passageway 96.

In a preferred embodiment utilizing fluid heating, a portion of shaft 312 of probe 370 is heatable by Joule-Thomson heating. Input passageway 372 is connectable to a source of compressed heating gas. Input passageway 372 transports compressed heating gas to a Joule-Thomson orifice 374. Compressed heating gas passing through orifice 374 expands into exhaust passageway 376, heats, and thereby heats outer wall 313 of shaft 312. Heated expanded heating gas is then exhausted from shaft 312 through exhaust passageway 376.

Probe 370 is thus operable to satisfy the requirements discussed above with respect to FIG. 10, in that operating tip 52 may be cooled to cryoablation temperatures, while shaft 312 is heated by expanding heating gas from Joule-Thomson orifice 374. Heating of shaft 312 protects tissues around shaft 312 both from cold exhaust gasses in exhaust passageway 96, and from cold induced by the cryoablation temperatures induced in tissues surrounding operating tip 52.

Attention is now drawn to FIG. 13, which is a simplified schematic of a cryoprobe 300 having an insulated shaft, according to an embodiment of the present invention.

FIG. 13 presents a cryoprobe 380 having a distal portion 320 implemented as a cryogenic operating tip 52, similar to that presented in FIG. 1 and in FIGS. 11 and 12, and discussed hereinabove. Probe 380 comprises a gas input passageway 78 operable to transport cooling gas, through a heat exchanging configuration 301, to a Joule-Thomson orifice 80 in operating tip 52, where it may be used to cool operating tip 52 as described hereinabove with respect to FIG. 1. Expanded gas from operating tip 52 is exhausted through exhaust passageway 96. Probe 370 of FIG. 13 is distinguished from probe 50 of FIG. 1, however, in that shaft 312 of probe 380 comprises an insulating element 382 which serves to insulate the outer surface 384 of shaft 312 from cold temperatures induced in the walls of gas exhaust passageway 96 by cold expanded cooling gasses passing therein. Insulating element 382 is preferably implemented as a vacuum-containing sheath 386 extending along at least a portion of shaft 312.

Probe 380 is thus operable to satisfy the requirements discussed above with respect to FIG. 10, in that operating tip 52 may be cooled to cryoablation temperatures, while external surfaces of shaft 312 are not substantially cooled by the cold cooling gasses, cooled by expansion in operating tip 52, which pass therein after cooling operating tip 52.

Figure 14:
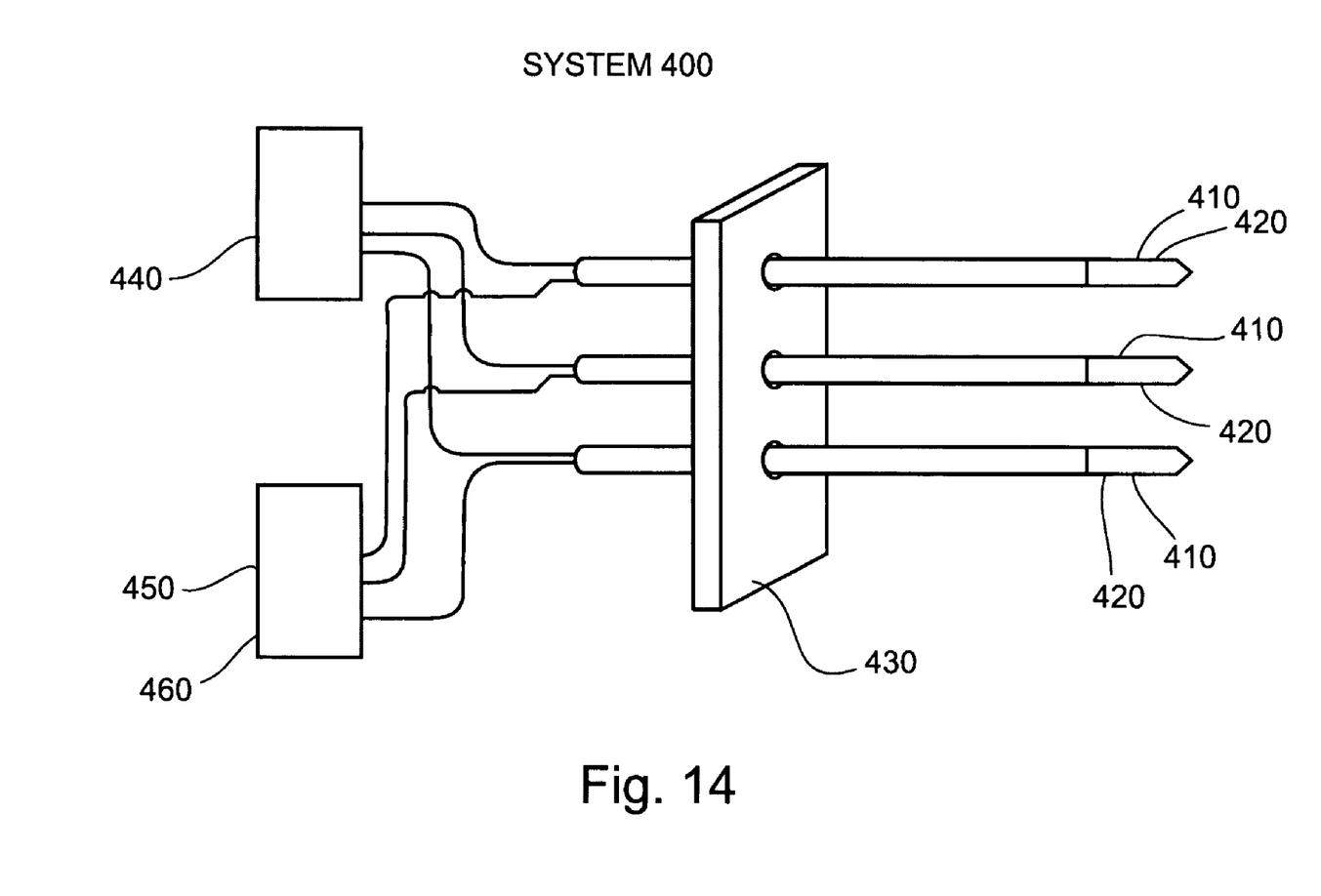
FIG. 14 is a simplified schematic of a system for cryoablation, comprising a positioning mechanism for positioning a plurality of cryoprobes with respect to a cryoablation target, and a plurality of cryoprobes having shafts designed and constructed to protect tissues adjacent to those shafts from damage during cryoablation, according to an embodiment of the present invention.

Attention is now drawn to FIG. 14, which is a simplified schematic of a system 400 for cryoablation, which system comprises a plurality of cryoprobes 410, each operable to cool a portion of a cryoablation target to cryoablation temperatures. At least some of cryoprobes 410 are cryoprobes 420 comprising shafts designed and constructed to protect tissues adjacent to those shafts from damage which would otherwise be caused by cold induced by flow of cold exhaust gases within those shafts. In a preferred embodiment of system 400, a cryoprobe placement mechanism 430 is implemented as a template similar to that presented hereinabove with particular reference to FIGS. 4-6. Cryoprobes 410 are preferably cooled by Joule-Thomson cooling, utilizing cooling gas provided by a gas source 440. Gas source 440 may be implemented as a manifold such as that presented in FIG. 2 and described hereinabove. Alternatively, gas source 440 may be a gas source designed and constructed to provide individualized control of supply of cooling gas to each cryoprobe 410.

In system 400, cryoprobes 420 are preferably implemented as probes 350, or as probes 370, or as probes 380, or as a combination thereof. If probes 370 are used, a heating fluid source 450 provides heating fluid to shaft portions of probes 350. Preferably heating fluid source 450 is a heating gas source 460 providing heating gas to probes 350, which heating gas, when expanded, provides Joule-Thomson heating in shafts of probes 350 as described hereinabove. Preferably, supply of heating fluid to probes 350 is individually controlled.

If system 400 is implemented utilizing probes 350, electrical power from an electrical power source (not shown) is used to provide power to shaft heaters within probes 370.

It is to be noted that probes 350, 370, and 380 present particular advantages when used in a context requiring a dense array of cryoprobes utilized for simultaneous cooling of diverse portions of a cryoablation target. Thus, system 400 is operable to enable use of a dense array of cryoprobes, operated to produce intense and rapid cooling throughout a prostate or other cryoablation target, while yet protecting tissues adjacent to shafts of deployed cryoprobes. Thus system 400 enables a clinical treatment methodology for prostate and similar cancers, the advantages of which were discussed in the background section hereinabove.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the s pacification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A cryoprobe having a proximal shaft and a distal operating tip, said distal operating tip comprises a cryocooler operable to cool to cryoablation temperatures tissues surrounding said distal operating tip, thereby cryoablating said tissues, said proximal shaft comprises
    (a) a cryogen exhaust lumen for exhausting cold cryogen from said cryocooler;
    (b) a heating element operable to heat at least a portion of an external wall of said proximal shaft during operation of said cryocooler, wherein said heating element is a fluid heating module, said heating module comprises a first passage for delivery of a fluid to a volume within said proximal shaft, and further comprises a second passage for exhausting said fluid from said volume of said proximal shaft; and (c) a separator which prevents gas transiting said exhaust lumen from directly contacting said heated portion of said external wall, thereby enabling to simultaneously both actively cool said distal operating tip and actively heat said external shaft wall portion without, during said simultaneous cooling and heating, exposing said heated shaft wall portion to contact with cold cryogen exhausting from said cryocooler.

2. The cryoprobe of claim 1, wherein said first passage is operable to deliver a pre-heated fluid to a portion of said proximal shaft.

3. The cryoprobe of claim 1, wherein said proximal shaft comprises a first Joule-Thomson orifice.

4. The cryoprobe of claim 3, wherein said first fluid input passage is operable to deliver a compressed heating gas to said first Joule-Thomson orifice.

5. The cryoprobe of claim 4, wherein said shaft comprises a first Joule-Thomson orifice and said operating tip comprises a second Joule-Thomson orifice.

6. The cryoprobe of claim 5, wherein said cryoprobe comprises a first gas input passage and a second gas input passage, said first gas input passage being operable to deliver compressed heating gas to said first Joule-Thomson orifice while said second gas input passage delivers compressed cooling gas to said second Joule-Thomson orifice.

7. The cryoprobe of claim 1, wherein said first passage is operable to deliver a compressed heating gas to said proximal shaft.

8. The cryoprobe of claim 1, wherein said proximal shaft comprises an insertable portion, which insertable portion is operable to be inserted into a body of a patient during cryoablation of tissues within said body of said patient, and wherein said heater is operable to heat all of said external wall of said insertable portion of said shaft during cooling operation of said cryocooler in said operating tip.

9. The cryoprobe of claim 1, operable to cool said distal operating tip to cryoablation temperatures and to heat said portion of said external wall of said proximal shaft at the same time.

* * * * *